United States Patent [19]
Watanabe

[11] Patent Number: 5,518,575
[45] Date of Patent: May 21, 1996

[54] SYSTEM FOR CONNECTING ONE FLEXIBLE TUBE TO ANOTHER FLEXIBLE TUBE

[75] Inventor: Takahiko Watanabe, Shizuoka, Japan

[73] Assignee: Terumo Kabushiki Kaisha, Tokyo, Japan

[21] Appl. No.: 215,820

[22] Filed: Mar. 22, 1994

[30] Foreign Application Priority Data

Jun. 16, 1993 [JP] Japan .................................. 5-169700

[51] Int. Cl.$^6$ ................................................ B29C 65/18
[52] U.S. Cl. ........................ 156/494; 156/499; 156/503; 156/543; 414/746.8; 414/751
[58] Field of Search ................................ 156/304.2, 539, 156/543, 503, 494; 264/288.4, 291; 425/392, 403.1, DIG. 53; 29/435, 280, DIG. 42; 226/88, 115, 126, 128, 134, 162; 901/39; 414/745.1, 746.8, 751, 910

[56] References Cited

U.S. PATENT DOCUMENTS

| | | | |
|---|---|---|---|
| 3,735,463 | 5/1973 | Merola | 29/DIG. 42 |
| 4,312,469 | 1/1982 | Nilsson | 226/162 |
| 4,369,779 | 1/1983 | Spencer | 128/213 A |
| 4,383,795 | 5/1983 | Wakamatsu et al. | 414/753 |
| 4,482,289 | 11/1984 | Inoba et al. | 414/751 |
| 4,548,537 | 10/1985 | Kubotera et al. | 414/746.8 |
| 4,704,886 | 11/1987 | Evert et al. | 264/291 |
| 4,714,400 | 12/1987 | Barnett et al. | 414/751 |
| 4,923,663 | 5/1990 | McMillan | 264/269 |
| 5,066,212 | 11/1991 | Moran, Jr. | 264/339 |
| 5,087,394 | 2/1992 | Keith | 264/291 |

FOREIGN PATENT DOCUMENTS

WO89/12019 12/1989 WIPO .............................. B66C 5/00

*Primary Examiner*—Steven D. Maki
*Attorney, Agent, or Firm*—Burns, Doane, Swecker & Mathis

[57] ABSTRACT

A tube loading apparatus for loading a flexible tube into a tube receiving section which can support the tube includes a head having a base, a pair of chucks mounted on the base and a driving mechanism for moving one of the chucks. The head is movable in the X and Y directions relative to the tube receiving section. Each of the chucks has a pair of holding members for holding the tube. One of the chucks is adapted to move in the X direction by the driving mechanism so as to change the distance between the chucks. The driving mechanism is driven when the tube is held by the holding members of the chucks, to increase the longitudinal distance of the tube while reducing the outer diameter of the tube. The thus deformed tube is inserted into the tube receiving section by keeping the deformed condition, and then the chucks are operated so as to release the tube. Accordingly, the tube can be automatically loaded into the tube receiving section.

10 Claims, 8 Drawing Sheets

5,518,575

SYSTEM FOR CONNECTING ONE FLEXIBLE TUBE TO ANOTHER FLEXIBLE TUBE

BACKGROUND OF THE INVENTION

1. Field of the Invention

This invention relates to a tube loading apparatus, and more particularly to a tube loading apparatus for loading a flexible tube into a receiving section such as a longitudinal groove.

2. Description of the Prior Art

There is known a tube connecting device in which ends of tubes to be connected are heated and melted and then the ends are connected by fusion, which is for example disclosed in U.S. Pat. No. 4,369,779.

The tube connecting device includes a pair of holders (blocks) which can hold two tubes to be connected in parallel with each other and a wafer (plate-like heating element) which is adapted to move across the tubes. In this device, two tubes are put into grooves formed in the respective holders so that these tubes are directed to the opposite directions and arranged in parallel to each other. Under these conditions, the wafer is heated and then moved to melt and cut off the tubes. Thereafter, one of the holders is shifted in the radial direction of the tube, and then the wafer is removed, to connect the predetermined tubes to each other by fusion.

In the meantime, in such a tube connecting device, the width of the respective groove formed in the holder is smaller than the outer diameter of the tube to be loaded. Therefore, conventionally, it was necessary to force the tube into the groove by a hand of an operator.

However, when the tube is forced into the groove, there is a case that the tube is imperfectly loaded within the groove since the tube is likely to be disengaged from the groove due to its resiliency. Such a manual operation takes lot of time and trouble, thus leading to difficulty in automating the tube connecting device.

SUMMARY OF THE INVENTION

In view of tile above described problem involved in the conventional tube connecting device, this invention has been made. Accordingly, an object of tile present invention is to provide a tube loading apparatus which can load a tube into a tube loaded section (tube receiving section) easily and surely.

In order to achieve the above mentioned object, the present invention is directed to tube loading apparatus for loading a flexible tube to a tube loaded section which can support the tube in contact with the outer surface thereof. The apparatus comprises two chucks which are spaced through a certain distance and can hold the tube at two different points thereof; and driving means for driving at least one of the chucks so as to change the distance between the chucks. The driving means is adapted to be driven under the condition that the tube is held by the chucks to increase the longitudinal distance of the tube while reducing the outer diameter thereof, and the thus deformed tube is inserted into the tube loaded section by keeping the deformed condition, and then the chucks are operated so as to release the tube.

According to tile present invention having the above structure, the tube is stretched to reduce its outer diameter, and the thus deformed tube is then loaded into the tube loaded section. Thereafter, the thus deformed tube is released to restore its original shape. Therefore, it is possible to load the tube into the tube loaded section easily and surely without causing any floating-up of the tube.

Further, according to the present invention, it is possible to load the tube into the tube loaded section automatically. Therefore, if the apparatus is applied to an automatic tube connecting device, all operations of the device including a tube loading step which loads a tube into a tube loaded section of the tube connecting device can be automated, thereby realizing automatic manufacturing process of blood derivatives in which a process for connecting tubes automatically is required.

In the present invention, preferably, each of the chucks is composed of a pair of holding members which can hold the tube therebetween. Further, preferably, the chucks and the driving means are provided on a head which is movable relative to the tube loaded section, and the head is preferably constituted so as to be able to move at least in the longitudinal direction of the tube and at least one direction perpendicular to the longitudinal direction.

Further, in the present invention, the tube loaded section is constituted from a groove. Preferably, the groove has a U-shaped cross section of which width is less than the outer diameter of the tube. Practically, the groove can be provided in an automatic tube connecting device which can connect flexible tubes by fusion.

Furthermore, in the present invention, preferably, the increasing ratio of the distance between said chucks is set between 102% and 130%, and the reducing ratio of the outer diameter of the tube is set between 75% to 98%.

Other objects, operations and advantages of the present invention will become more apparent from the following descriptions of the preferred embodiment which is made in conjunction with the accompanying drawings.

DETAILED DESCRIPTION OF THE PREFERRED EMBODIMENT

Hereinbelow, a preferred embodiment of this invention will be described with reference to the accompanying drawings.

Figure 1:
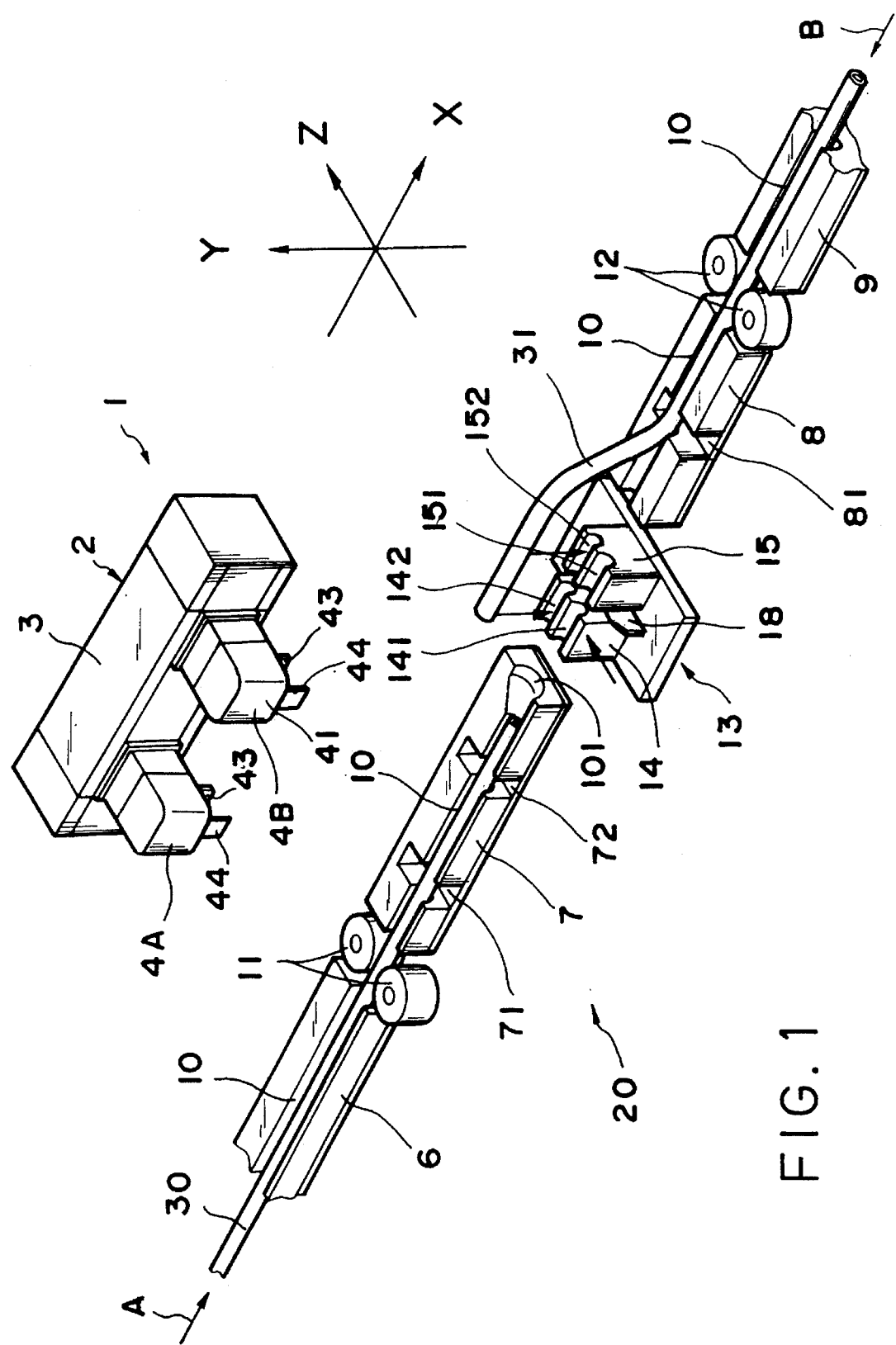
FIG. 1 is a perspective view of an embodiment of a tube loading apparatus according to the present invention.

FIG. 1 is a perspective view which shows an embodiment of the tube loading apparatus according to the present invention. The tube loading apparatus 1 shown in the drawing is an apparatus for loading flexible tubes 30, 31 which are to be carried along predetermined carrier paths into a tube loaded section which is described hereinbelow. This tube loading apparatus 1 has a head 2 which includes a block-like base 3, two chucks 4A and 4B mounted on the base 3 for pinching the tube 30 or tube 31, and a driving means 5 for moving the chuck 4B (shown in FIGS. 2 and 3).

The chucks 4A and 4B are arranged on the front surface of the base 3, in which the chuck 4A is fixedly mounted on the base 3 while the chuck 4B is mounted on the base 3 so as to be able to move in the X direction in FIG. 1. In accordance with the movement of the chuck 4B, the distance between the chucks 4A and 4B changes.

In this regard, if tile distance between the chucks 4A and 4B (which is measured between the centers of the holding members of the respective chucks 4A and 4B described hereinbelow) before pinching the tube 30 is L1 and the distance between the chucks 4A and 4B which is measured under the condition that the chucks 4A and 4B pinch the tube 30, respectively and then the chuck 4B is moved toward such a direction that the chuck 4B is apart from the chuck 4A to stretch the tube 30 is L2, it is preferable that the increasing ratio of the distance between the chucks 4A and 4B, that is L2/L1 becomes 102%–130%, and more preferably 105%–115%. By doing so, the outer diameter of the tube 30 is reduced into 75%–98% of the original outer diameter of the tube and in particular 80%–95% of the original outer diameter so that it is possible to load the tube into the tube loaded section easily and surely.

In this regard, L2 is determined to be a value in which the total length of the tube loaded section in X the direction is included between the chucks 4A and 4B.

Figure 2:
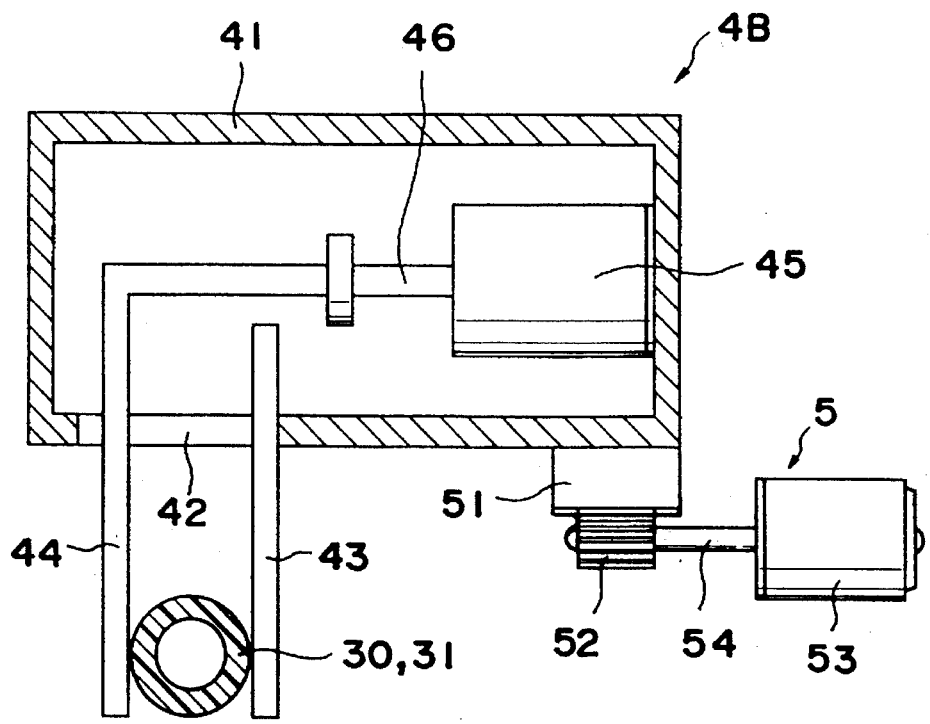
FIG. 2 is a sectional view which shows one operational condition of a chuck of the tube loading apparatus according to the present invention.
Figure 3:
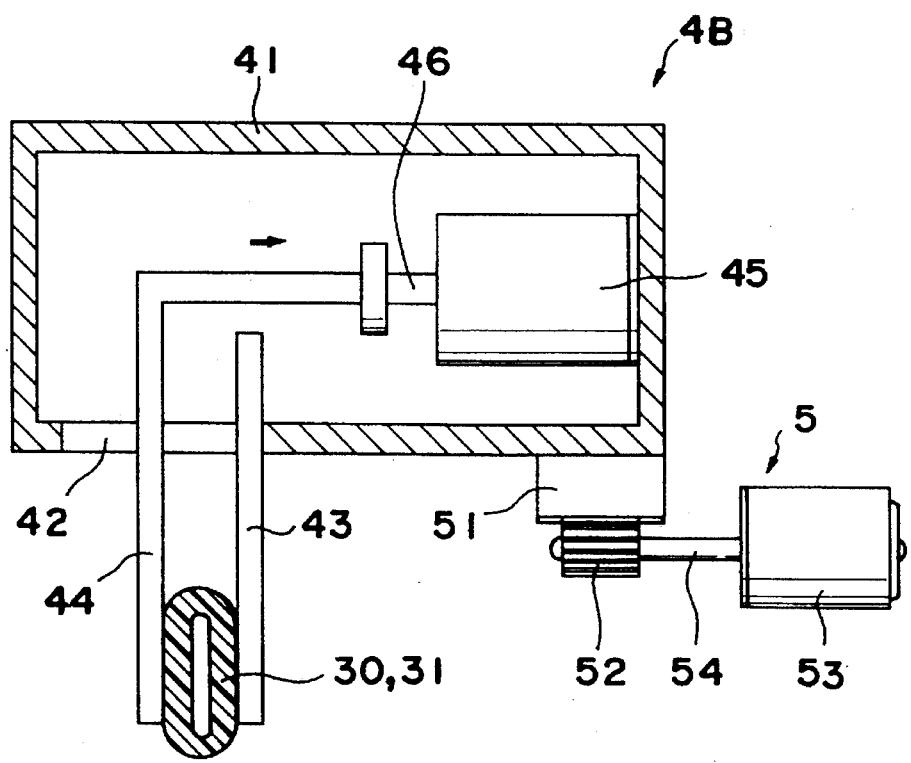
FIG. 3 is a sectional view which shows a different operational condition of the chuck of the tube loading apparatus according to the present invention.

FIGS. 2 and 3 are partially sectional side views which show the structure of the chuck 4B, respectively. As shown in the drawings, the chuck 4B comprises a casing 41 in which an opening 42 is formed, a pair of plate-like holding members 43 and 44 for holding or pinching tile tubes 30 and 31 therebetween, and a driving means 5 for driving the holding member 44, in which the holding members 43 and 44 are protruded to the outside of the casing through the opening 42.

The holding member 43 is fixedly mounted on the casing 41, while the holding member 44 is movable in the Z direction in FIG. 1. The holding member 44 is bent into an L-shape at the base end thereof (upper side in FIG. 2), and this bent end portion is coupled to a tip portion of a plunger 46 of a solenoid 45 which is fixedly disposed within the casing 41.

As shown in FIG. 2, when the solenoid 45 is not energized, the plunger 46 is extended. As a result, the holding members 43 and 44 are spaced to such an extent that the tube 30 can be inserted or interposed therebetween.

As shown in FIG. 3, when the solenoid 45 is energized, the plunger 46 is retracted. In accordance with the movement of the plunger 46, the holding member 44 is moved so as to approach the holding member 43, thereby enabling the tube to be pinched or held between the holding members 43 and 44.

The chucking pressure generated by the holding members 43 and 44 to hold the tube 30 is preferably determined to such an extent that no slip is caused between the tube and the holding members and any damage such as break or crack or nonrestorable deformation is not given to the tube when the tube 30 is stretched by the holding members 43 and 44 until the stretching ratio described above.

The shape of the respective holding members 43 and 44 is not limited to the flat shape as shown in FIGS. 2 and 3. It is also possible to adopt other modifications which are shown in FIGS. 4 to 9.

Figure 4:
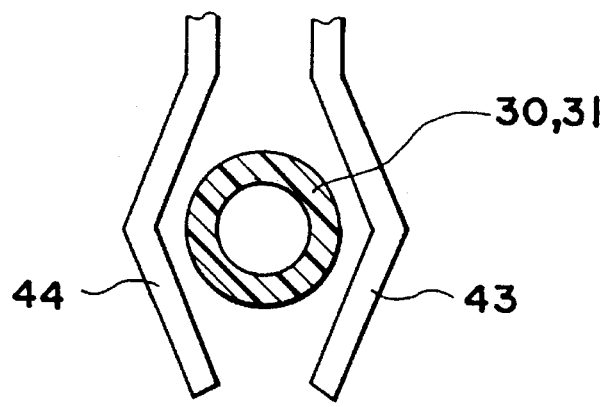
FIG. 4 is a side view which shows a first modification of tip portions of holding members of the chuck of the tube loading apparatus according to the present invention.

In a first modification shown in FIG. 4, each of the tip portions of the respective holding members 43 and 44 is also roughly formed into an angular shape of which the apex is outwardly protruded, respectively.

Figure 5:
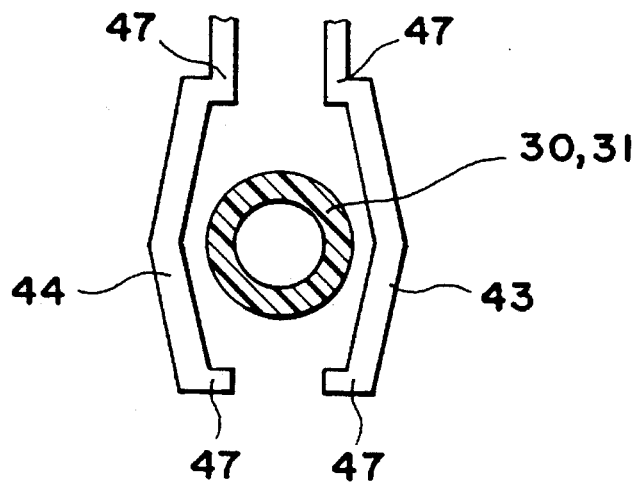
FIG. 5 is a side view which shows a second modification of the tip portions of the holding members.

In a second modification shown in FIG. 5, each of the tip portions of tile respective holding members 43 and 44 is roughly formed into an angular shape of which the apex is outwardly protruded. Each of the tip portions has a base and tip ends 47 which are inwardly bent, respectively. The opposing base and tip ends 47 of the tip portions of the opposing holding members 43 and 44 are brought into contact with each other, to regulate a distance of a space defined when the opposing holding members 43, 44 are in the closest position (hereinafter, referred to "the shortest space distance").

Figure 6:
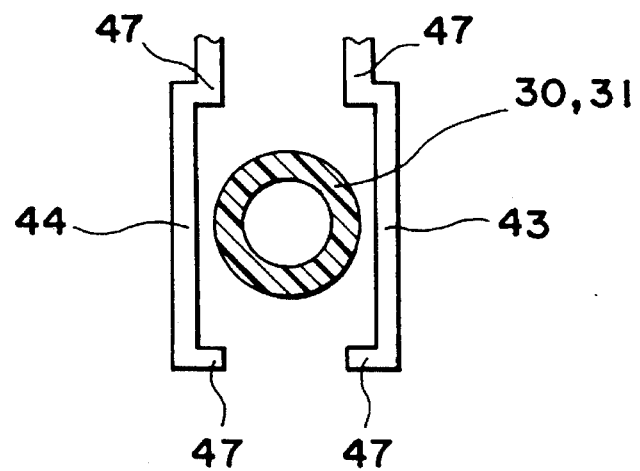
FIG. 6 is a side view which shows a third modification of the tip portions of the holding members.

In a third modification shown in FIG. 6, each of the tip portions of the respective holding members 43 and 44 is formed into a roughly C-shape having a base and tip ends 47, respectively. The opposing base and tip ends 47 of the tip portions of the opposing holding members 43 and 44 are brought into contact with each other, to regulate the shortest space distance between the holding members 43, 44.

Figure 7:
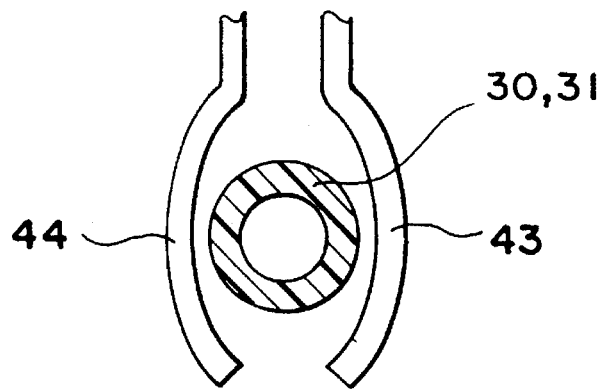
FIG. 7 is a side view which shows a fourth modification of the tip portions of the holding members.

In a fourth modification shown in FIG. 7, each of the tip portions of the respective holding members 43, 44 is roughly formed into an arc-shape, respectively.

Figure 8:
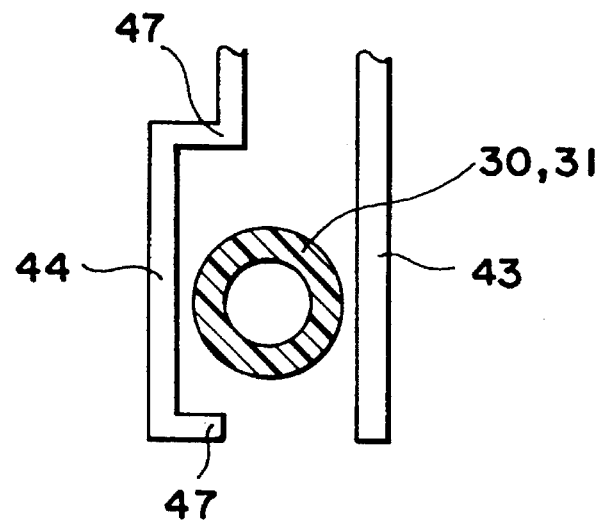
FIG. 8 is a side view which shows a fifth modification of the tip portions of the holding members.

In a fifth modification shown in FIG. 8, one of the holding members 43 is formed into a straight shape, while the tip portion of the other holding member 44 is roughly formed into a C-shape having a base and tip ends. The base and tip ends 47 of the other holding member 44 are adapted to abut with the inner surface of the holding member 43, to regulate the shortest space distance.

Figure 9:
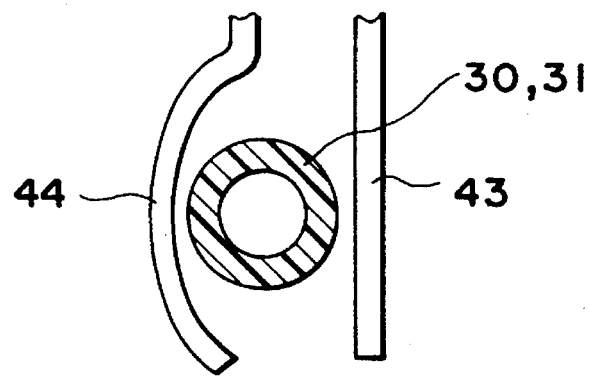
FIG. 9 is a side view which shows a sixth modification of the tip portions of the holding members.

In a sixth modification shown in FIG. 9, one of the holding members 43 is formed into a straight shape, while the tip portion of the other holding member 44 is formed into an arc-shape.

In connection with these modifications, it should be noted that it is possible to form fine uneven (concave and convex) portions on the inner surfaces of the respective holding members 43, 44 (on the portions to which the tube 30 is brought into contact) or to provide other material having relatively large frictional resistance such as any rubbers on the inner surfaces thereof. By doing so, it becomes possible to prevent slip of the tube from occurring when the tube 30 is stretched or extended under the condition that the tube 30 is pinched between the inner surfaces of the opposing holding members 43, 44.

The driving means 5 for moving the chuck 4B is composed of a rack gear 51 fixedly mounted at the underside of a casing 41, a motor 53 and a pinion gear 52 which is fixed to a tip portion of a rotary axis 52 of the motor 53 and which is in meshing engagement with the rack gear 51. When the motor 53 is driven, the pinion gear 52 is rotated in a predetermined direction. In accordance with tile rotation of the pinion gear 52, the rack gear 51 is moved toward its longitudinal direction, that is the direction perpendicular to the sheet surface of FIG. 2 (X direction in FIG. 1).

The motor 53 is rotatable in either of the forward and reverse directions, so that the chuck 4B can be moved reciprocally in the direction perpendicular to the sheet surface of FIG. 2 (X direction in FIG. 1).

The structure of the chuck 4A is the same as that of the chuck 4B described above, except for the driving means 5.

In this regard, it should be noted that the structure of the respective chucks 4A and 4B is not limited to the above structure. For example, it is also possible to constitute the holding member 44 so as to be moved by any other driving source such as an air cylinder or a hydraulic cylinder other than a solenoid, and further it is also possible to use them as the driving source and the driving mechanism for the driving means 5 which drives the chuck 4B.

Further, in the above described structure, only the chuck 4B is adapted to be movable. However, it is of course possible to design a both the chucks 4A and 4B to be movable so as to be able to change the distance between the chucks.

The above described head 2 which is composed of the base 3, the chucks 4A and 4B and the driving means 5 is movable in two-dimensional directions, that is in the X direction in FIG. 1 and the Y direction perpendicular to the X direction, by utilization of a known X-Y stage.

As one practical example of the X-Y stage, the following structure can be adopted.

Figure 10:
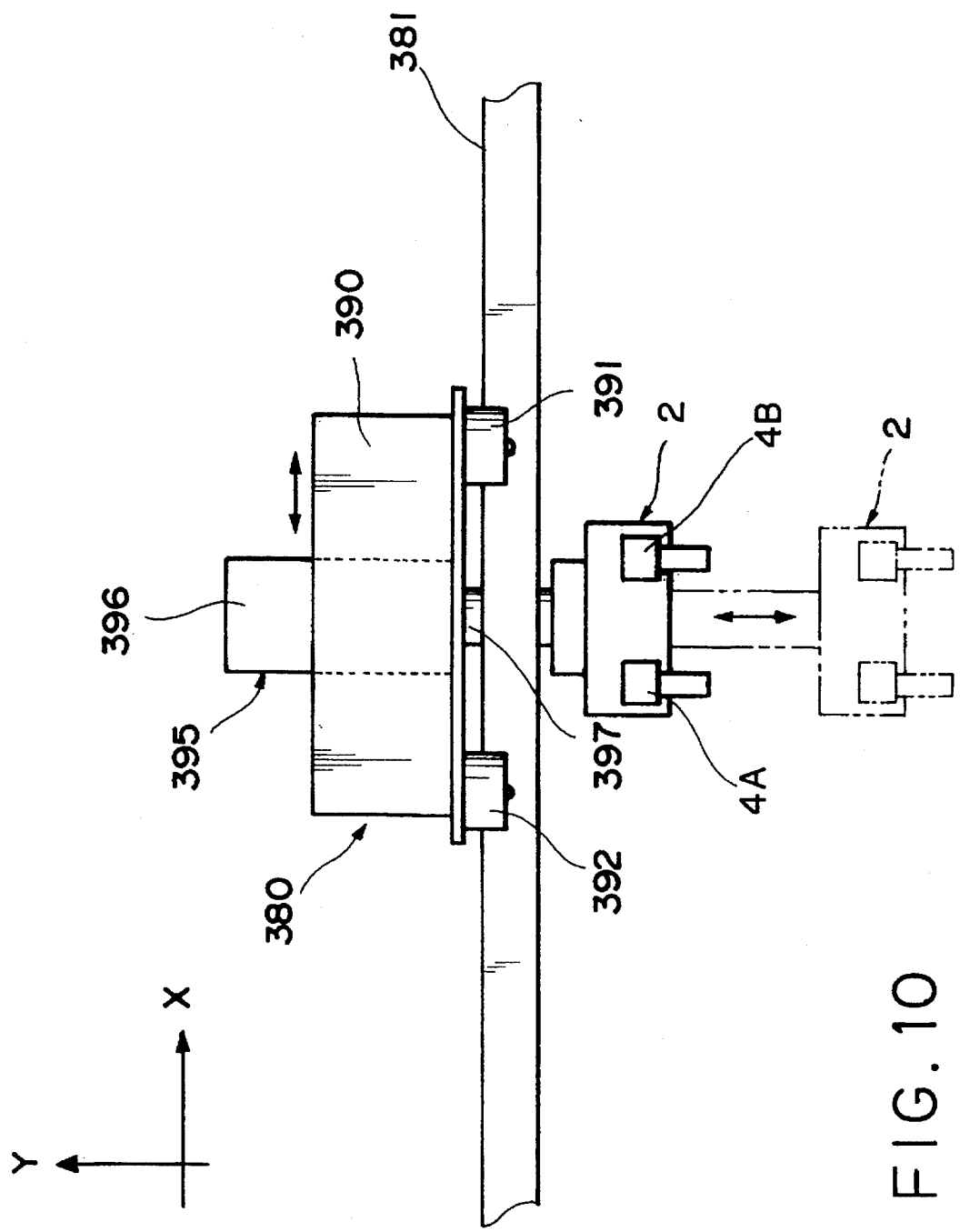
FIG. 10 is a front view which shows one example of a head moving mechanism of the tube loading apparatus according to the present invention.

Namely, as shown in FIG. 10, in this X-Y stage, the head 2 composed of the base 3, the chucks 4A and 4B and the driving means 5 is constituted to be movable in two-dimensional directions, that is in the X direction in the drawing and the Y direction normal to the X direction, by a moving mechanism 380.

The moving mechanism 380 includes a carrier rail 381, a movable body 390 and an elevating device 395. The carrier rail 381 is arranged parallel with the longitudinal direction of the tube in the tube loaded section, that is the X direction described above.

The movable body 390 is movably disposed on the carrier rail 381 in such a manner that it can travel along the carrier rail 381 reciprocally. In the movable body 390, there is provided two pairs of rollers 391 and 392 each of which interpose the carrier rail 381 therebetween, respectively, and a motor for rotating the rollers 391 and 392 (not shown). This motor is rotatable in forward and reverse directions. Therefore, when the rollers 391 and 392 are rotated in accordance with the rotational motion of the motor, the movable body 390 can be moved along the carrier rail 381 reciprocally within a predetermined range.

In the movable body 390, there is also provided the elevating device 395. The elevating device 395 is composed of a cylinder 396 such as an air cylinder or a hydraulic cylinder which is arranged in the vertical direction, and a piston rod 397 which is retractable in accordance with the operation of the cylinder 396. The head 2 is mounted to the lower end of the piston rod 397.

In the moving mechanism 380 having the above structure, the head 2 can be moved in the X direction in FIG. 10 in accordance with the movement of the movable body 390 and it can be also moved in the Y direction in FIG. 10 (up and down direction) in accordance with the retracting movement of the piston rod 397.

In this regard, the head 2 can be adapted to be movable in three-dimensional directions, that is in X, Y and Z directions.

In this embodiment, the movements of the head 2, the chuck 4B and the holding members 43 and 44 may be controlled by commands fed from an operation panel (not shown). However, it is preferable to control them by a programmed sequence control.

As shown in FIG. 1, a tube carrying system 20 is provided below the tube loading apparatus 1. In this tube carrying system 20, there is disposed a plurality of tube carrier rails along the carrier paths for the tubes 30 and 31 which extend in the X direction in the drawing. In more detail, in the structure shown in FIG. 1, carrier rails 6, 7, 8 and 9 are arranged in this order from an upstream side of the tube carrying direction of the tube 30 indicated by the arrow A (hereinafter, referred to as "upstream side") to a downstream side of the tube carrying direction.

In each of these tube carrier rails 6, 7, 8 and 9, there is formed a groove 10 having a U-shaped cross section for instance along its longitudinal direction. These grooves 10 serve as a carrier passage through which the tube 30 is to be carried. In this case, the width of the groove is slightly larger than the original outer diameter of the tube 30 to be carried.

Further, in order to absorb dislocation of the tube 30 in the Z direction which is likely to be caused when a holder 14 is shifted upon connection of the tubes 30 and 31, the end portion 101 of the groove 10 at the downstream side thereof is formed widely.

Furthermore, at the middle portion of the carrier rail 8, there is formed a notch 81 to which the holding members 43 and 44 of the chuck 4B can be inserted.

Between the end portion of the carrier rail 6 at the downstream side thereof and the end portion of the carrier rail 7 at the upstream side thereof, there is provided a pair of rollers 11 which are opposite to each other through the tube carrier path of the tube 30. A driving means such as a motor for instance (not shown) is coupled to the rollers 11 to rotate at least one of the rollers 11. The tube 30 is carried by rotating the rollers 11 by the driving means 5 under the condition that the tube 30 is pinched between the rollers 11.

Further, between the end portion of the carrier rail 8 at the downstream side thereof and the end portion of the carrier rail 9 at the upstream side thereof, there is provided a pair of rollers 12 in the same manner as the rollers 11 described above.

Between the end portion of the carrier rail 7 at the downstream side thereof and the end portion of the carrier rail 8 at the upstream side thereof, there is provided the tube connecting device 13 for connecting the tubes to each other by heating and melting the tubes.

Figure 11:
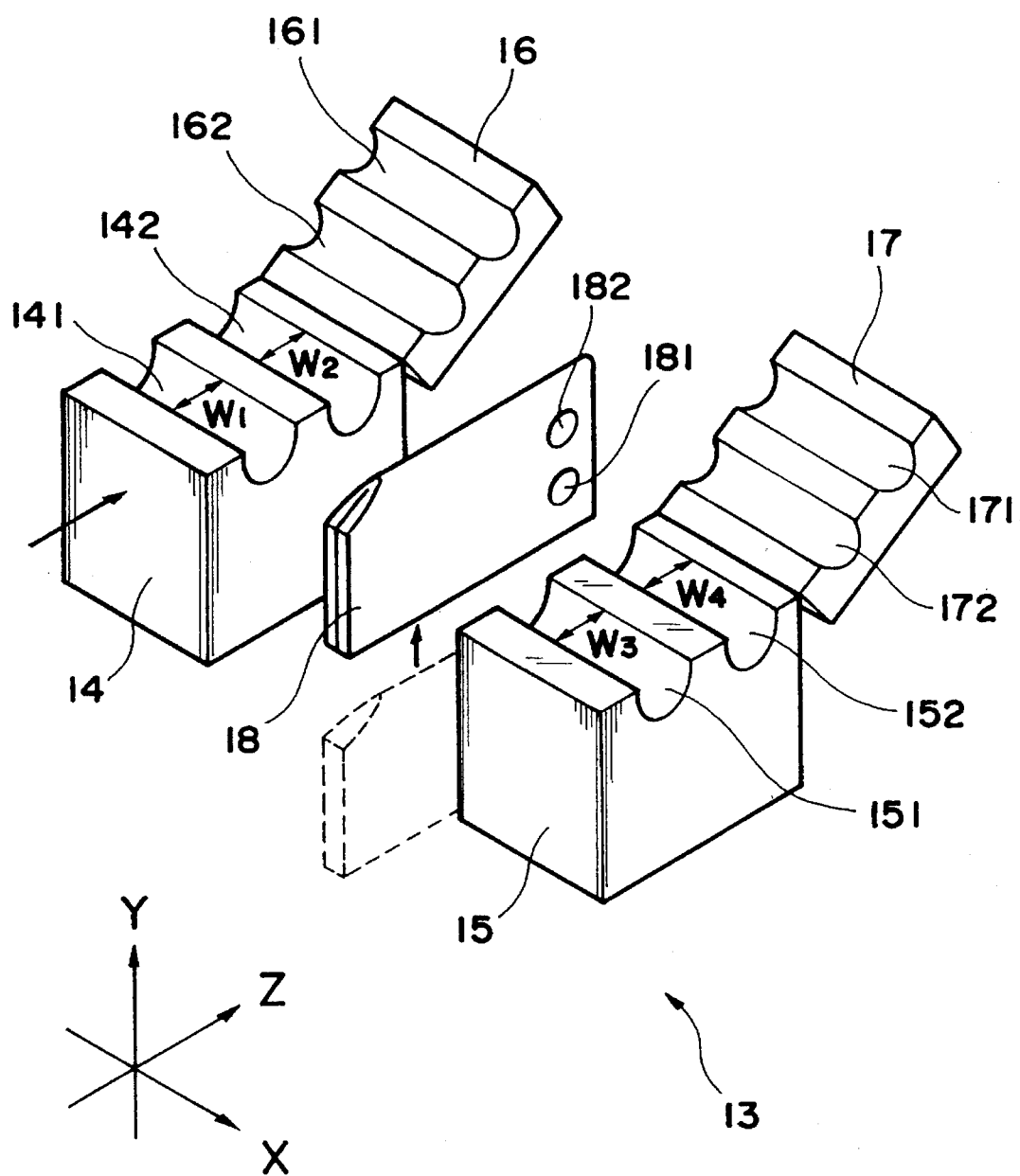
FIG. 11 is a perspective view which shows one example of a tube connecting device which is used in conjunction with the tube loading apparatus according to the present invention.

FIG. 11 is a perspective view showing a main part of the tube connecting device 13. As shown in the drawing, the tube connecting device 13 is composed of a pair of holders 14 and 15 and a wafer (plate-like heating element) disposed between the holders 14 and 15.

The holder 15 is fixedly mounted with respect to the tube connecting device 13, while the holder 14 is mounted movably in the Z direction by a driving means not shown.

On the upper surface of the holder 14, there are formed two grooves 141 and 142 which have U-shaped cross section, respectively, and are arranged parallel to each other. Further, on the upper surface of the holder 15, there are also formed two grooves 151 and 152 which have a shaped cross section, respectively, and are arranged parallel to each other. In this embodiment, these grooves 141, 142, 151 and 152 serve as the tube loaded section (tube receiving section), respectively.

Before the tubes 30 and 31 are loaded, the grooves 141 and 151 are positioned coaxially with respect to the grooves 10 formed in the carrier rails 6 and 7, and the grooves 142 and 152 are positioned coaxially with respect to the grooves 10 formed in the carrier rails 8 and 9.

The widths W1 and W3 of the grooves 141 and 151 are preferably determined so as to be smaller than the original outer diameter of the tube 30, respectively and larger than the reduced outer diameter of the tube 30 under the stretched condition. Further, the widths W2 and W4 of the grooves 142 and 152 are also determined so as to be smaller than the original outer diameter of the tube 31, respectively and larger than the reduced outer diameter of the tube 31 under the stretched condition.

On the upper side of the holders 14 and 15, covers 16 and 17 are pivotally mounted, respectively. On the inner surfaces of these covers 16 and 17, there are formed grooves 161, 162 and 171, 172 which correspond to the grooves 141, 142 and 151, 152, respectively.

In this regard, it should be noted that the shape of the grooves is not limited to the U-shape described above, and other shapes such as C-shape or V-shape can be adopted.

Between the holders 14 and 15, the wafer 18 which is replaceable with other wafers is disposed so as to be able to move in the Y direction (up and down direction in FIG. 11).

This wafer 18 is formed by folding a metallic plate such as a copper plate into two and putting a resistive layer for heat generation having a desired pattern (not shown) therebetween through insulating layers. The terminals 181 and 182 of the resistive layer are exposed from openings formed in the metallic plate, respectively. Preferably, the wafer 18 is disposable after a single use for the tube connection.

Although not shown in the drawing, it is possible to form tube pinching portions at the end portions of the holders 14 and 15 at the side of the wafer 18 for pressing the tubes 30 and 31 to close inner passage thereof when the covers 16 and 17 are closed.

In the tube connecting device 13, the downstream side of the tube 30 is loaded into the grooves 141 and 151 of the holders 14 and 15, and the upstream side of the tube 31 is loaded into the grooves 142 and 152, respectively by the tube loading apparatus 1 described above. Thereafter, the covers 16 and 17 are closed. Under the condition, the wafer 18 which has been heated to 260° C.–320° C. by supplying electric current to the terminals 181 and 182 is lifted to melt the tubes and then cut off them. Thereafter, the holder 14 is shifted in the Z direction to such an extent that corresponds to the distance measured between the centers of the grooves 141 and 142 so that the cut portions of the tubes 30 and 31 face each other. Thereafter, the wafer 18 is lowered and then removed, and thereby the tubes 30 and 31 are connected by fusion.

In this case, the tip portions of the downstream side of the tube 30 and the tip portion of the upstream side of the tube 31 may be closed by fusion. If desired, it is possible to connect the tubes 30 and 31 under sterile condition.

The purpose of use of the tubes 30 and 31 is not limited to a specific purpose. For example, the tubes can be used as tubes to be connected to various bags such as a blood bag, blood collecting bag, blood component bag, blood tranfusion bag, dialysis bag, liquid discharge bag, urine introducing bag, etc. Further, the tubes can also be used as tubes for constituting a part of a blood collecting apparatus or a blood transfusing apparatus or tubes for constituting circulation circuits of blood or blood component for an artificial lung or an artificial dialysis system, etc. Furthermore, the tubes can also be used as tubes for various catheter tubes to be inserted into a living body such as a digestive canal, blood vessel, urethral canal, bile duct, etc. or artificial internal tubular organs such as artificial blood vessel retained in a living body.

As a material of the tubes 30 and 31, it is possible to selectively use one or more of various materials including polyvinyl chloride; polyolefin such as polyethylene, polypropylene, EVA; polyester such as PET or PBT; polyurethane; polyamide; silicone; or thermoplastic elastomer such as polyester elastomer, polyamide elastomer, styrene-butadiene copolymer. However, among these materials, the polyvinyl chloride is particularly preferable as the material of the tube 30, since it is most suitable when the mass production process of the tubes is automatized.

Further, although the dimension of the respective tubes 30 and 31 is not limited specifically, the preferable dimension of the respective tubes 30 and 31 is about 2 mm to 40 mm and more preferably 3 mm to 9 mm at the outer diameter thereof.

The tube carrying system 20 as described above is suitable when tubes connected to bags such as a blood bag or a blood components correcting bag are carried to predetermined destinations, and thus carried tubes are closed (by fusion), cut off, or connected to other tubes or other members (such as connectors or needle) at the destinations. If such a tube carrying system 20 is used for changing connecting pattern among tubes connected to some bags so as to be able to transfer each blood component to the respective bags it becomes possible to automatize manufacturing process of blood derivatives.

Figure 12:
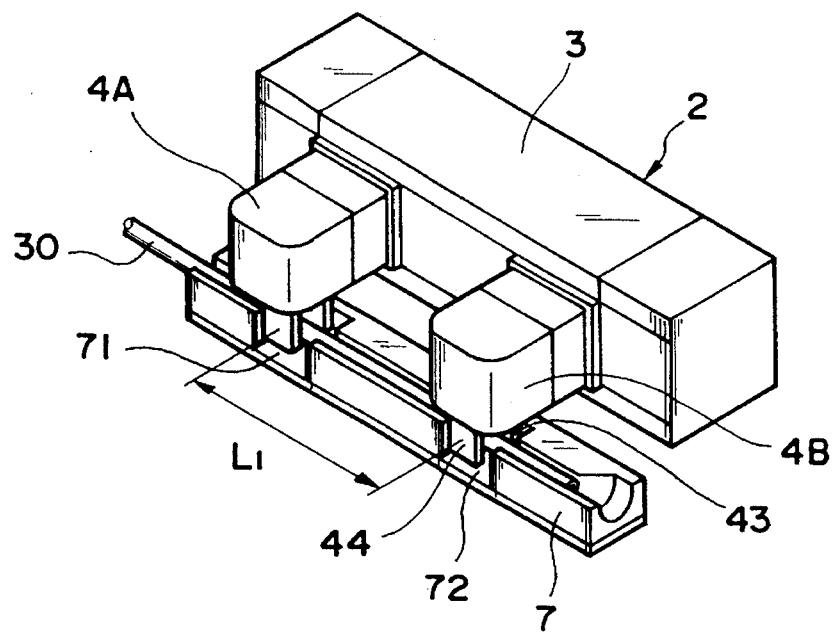
FIG. 12 is a perspective view which shows a step for loading a tube by the tube loading apparatus according to the present invention.
Figure 13:
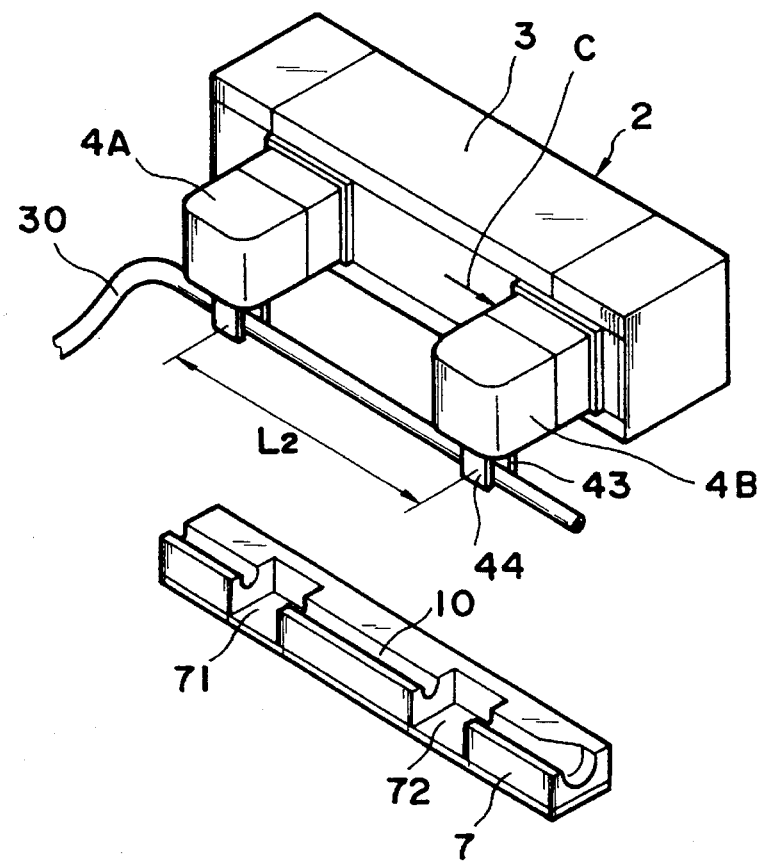
FIG. 13 is a perspective view which shows other step for loading a tube by the tube loading apparatus according to the present invention.
Figure 14:
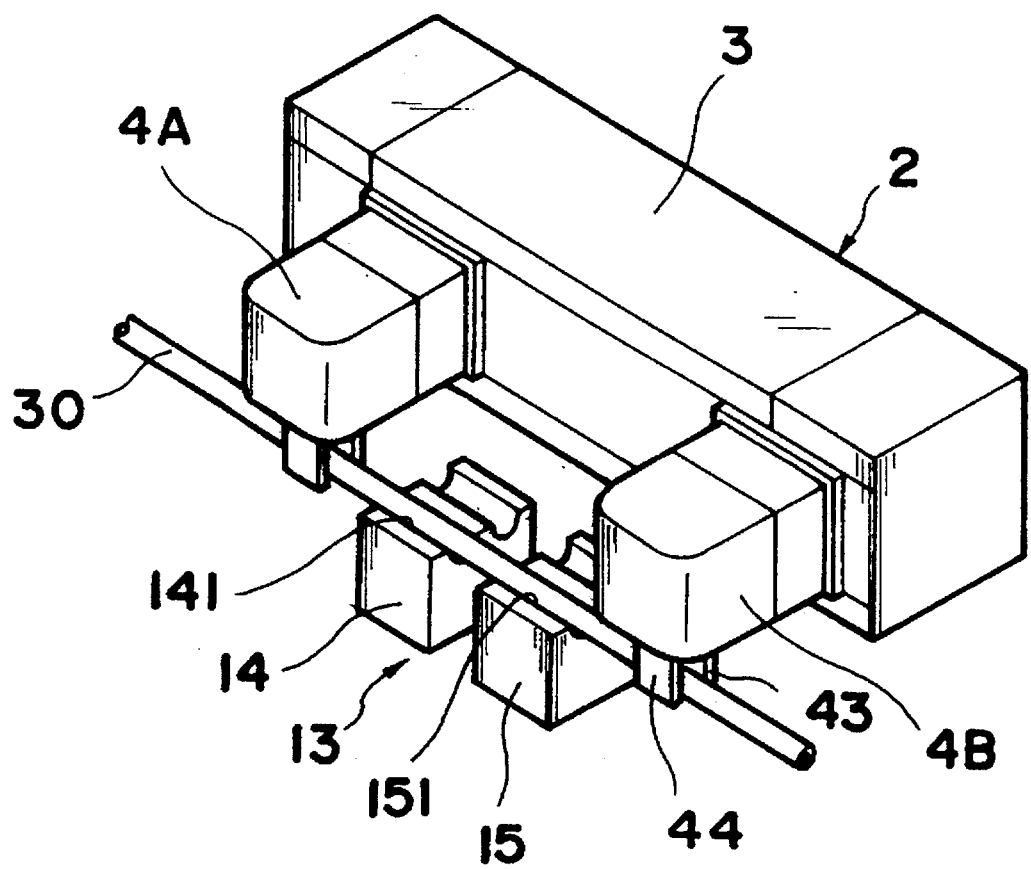
FIG. 14 is a perspective view which shows other step for loading a tube by the tube loading apparatus according to the present invention.

Hereinafter, the tube loading process and the tube connecting process performed by the tube loading apparatus 1 will be described. FIGS. 12, 13 and 14 are perspective views which show different steps for loading the tube to the tube loaded section by the tube loading apparatus 1, respectively. Hereinbelow, each step will be explained with reference to these drawings.

[1] As shown in FIG. 1, the tube 30 is carried from the upstream side to the downstream side in the X direction (direction indicated by the arrow A in FIG. 1) along the grooves 10 formed in the carrier rails 6 and 7 by rotating the rollers 11. When the tip portion of the tube 30 reaches and then passes the notch 72, the rotation of the rollers 11 is stopped.

[2] As shown in FIG. 1, the tube 31 is carried from the downstream side to the upstream side in the X direction (direction indicated by the arrow B in FIG. 1) along the grooves 10 formed in the carrier rails 9 and 8 by rotating the rollers 12. When the tip portion of the tube 31 is protruded from the end surface of the upstream side of the carrier rail 8 for a predetermined length, the rotation of the rollers 12 is stopped.

[3] As shown in FIG. 1, the head 2 of the tube loading apparatus 1 is positioned above the carrier rail 8, in which the chucks 4A and 4B are kept in the approached condition (the distance between the chucks 4A and 4B=L1) and the holding members 43 and 44 of the respective chucks 4A and 4B are apart from each other to allow insertion of the tube 30 therebetween.

[4] As shown in FIG. 12, the head 2 is lowered in such a manner that the holding members 43 and 44 of the respective chucks 4A and 4B are inserted into the corresponding notches 71 and 72. By doing so, the tube 30 is inserted or interposed between the holding members 43 and 44 of the respective chucks 4A and 4B.

[5] The solenoid incorporated in the respective chucks 4A and 4B is energized, respectively, to move the holding member 44 so that it approaches the holding member 43. By doing so, the tube 30 is held or pinched by the two pair of the holding members 43 and 44 at the spaced two points thereof. Thereafter, the head 2 is elevated to the original position to lift the tube 30.

[6] As shown in FIG. 13, under the condition that the tube 30 is pinched or held by the chucks 4A and 4B, the driving means 5 is operated to move the chuck 4B away from the chuck 4A (the direction indicated by the arrow C in FIG. 13). By doing so, the tube 30 held between the chucks 4A and 4B is stretched and then the outer diameter thereof is reduced.

[7] The head 2 is moved in the X direction and Y direction (downward direction in FIG. 1) by keeping the stretched condition and then the tube 30 between the chucks 4A and 4B is inserted into the tube loaded section, that is the grooves 141 and 151 of the holders 14 and 15 as shown in FIG. 14. In this case, since the outer diameter of the tube 30 between the chucks 4A and 4B has been reduced to such an extent as described above, the tube 30 can be easily inserted into the grooves 141 and 151 without any resistance, and therefore no floating-up of the tube will occur.

[8] The solenoid incorporated In the respective chucks 4A and 4B is disenergized, respectively, to move the holding member 44 away from the holding member 43, thereby releasing the tube 30 pinched by the holding members 43 and 44. By doing so, the stretched tube 30 is restored into its original shape due to its resiliency. When the tube 30 is so restored, the outer diameter of the tube 30 increases within the grooves 141 and 151, so that the tube 30 can be lightly fitted within the grooves 141 and 151.

[9] The head 2 is moved in the Y direction (upward direction in FIG. 1) and the X direction so as to be positioned above the carrier rail 8, and the chuck 4B is then moved toward the direction that it approaches the chuck 4A for a predetermined distance by driving the driving means 5 to the reverse direction opposite to the above rotational direction, thereby restoring its original condition (the distance between the chucks 4A and 4B=L1).

In a case where the head 2 is movable in the X, Y and Z directions, the head 2 is positioned above the carrier rail 8 by moving the head 2 in the Y direction (upward direction in FIG. 1) and the X direction as well as the Z direction to such an extent that corresponds to the distance between the centers of the grooves 141 and 142.

[10] Thereafter, the head 2 is lowered in such a manner that the holding members 43 and 44 of the respective chucks 4A and 4B are inserted into the notch 81 and the space defined between the end surface of the upstream side of the carrier rail 8 and the tube connecting device 13, respectively. By doing so, the tube 31 is inserted or interposed between the holding members 43 and 44 of the respective chucks 4A and 4B.

[11] In the same manner as the step [5], the tube 31 is pinched by the two pairs of the holding members 43 and 44 at the spaced points thereof, and then the head 2 is elevated to the original position to lift the tube 31.

[12] In the same manner as the step [6], the chuck 4B is moved away from the chuck 4A (direction indicated by the arrow C in FIG. 13), to stretch the tube 31 held between the chucks 4A and 4B.

[13] In the same manner as the step [7], the head 2 is moved in the X and Y directions by keeping the stretched condition of the tube 31 and then the tube 31 between the chucks 4A and 4B Is inserted into the tube loaded section, that is the grooves 142 and 152 of the holders 14 and 15. In this case, since the outer diameter of the tube 31 between the chucks 4A and 4B has been reduced to such an extent as described above, the tube can be easily inserted into the grooves 142 and 152 without any resistance, and therefore no floating-up of the tube will be happened.

[14] In the same manner as the step [8], the holding member 44 is moved away from the holding member 43, to release the tube 31 pinched between the holding members 43 and 44 of the respective chucks 4A and 4B. By doing so, the stretched tube 31 is restored into its original shape due to its resiliency. When the tube is so restored, the outer diameter of the tube 31 increases within the grooves 142 and 152, so that the tube 31 can be tightly fitted within the grooves 142 and 152.

[15] The head 2 is moved in the Y direction (upward direction in FIG. 1) and the X direction so as to be positioned above the carrier rail 7, and the chuck 4B is then moved toward the chuck 4A for a predetermined distance by driving the driving means 5 to the reverse direction opposite to the above rotational direction, thereby restoring the head to its original condition (the distance between the chucks 4A and 4B=L1). By doing so, the head 2 is in a waiting condition for the next tube loading operation.

In a case where the head 2 is movable in the X, Y and Z directions, the head 2 is positioned above the carrier rail 7 by moving the head 2 in the Y direction (upward direction in FIG. 1) and the X direction as well as the opposite Z direction to such an extent that corresponds to the distance between the centers of the grooves 141 and 142.

[16] The tubes 30 and 31 which have been loaded to the tube loaded sections by the tube loading apparatus 1 are connected to each other by the tube connecting device 13. In more detail, first the covers 16 and 17 are closed. Next, the wafer 18 which has been heated by supplying electrical current to the terminals 181 and 182 is raised to melt and then cut off the tubes 30 and 31. Thereafter, the holder 14 is shifted in the Z direction to such an extent that corresponds to the distance between the centers of the grooves 141 and 142 so that the cut off end of the respective tubes 30 and 31 face with each other, and then the wafer 18 is lowered and removed, thereby connecting the ends of the tubes 30 and 31 by fusion.

In this step, there is a case that the connected portion between the tubes 30 and 31 is flattened since its inner surfaces are fused and therefore the tube is closed at that position. In such a case, therefore, the deformed connected portion between the tubes 30 and 31 is restored by squeezing it in order to keep the inner passage of the connected tube open.

After the tubes 30 and 31 are so connected with each other, the cut off tip portions of the tubes are removed from the grooves 151 and 142, and then thrown out. In addition, the used wafer 18 is replaced with a new wafer 18 for the sake of the next tube connection.

In the above, the tube loading apparatus according to the present invention has been described with reference to the structural examples shown in the attached drawings. However, the present invention is no limited to these structural examples. For example, the tube loaded section is not limited to one formed in the tube connecting device as described above. This apparatus can be applied to other tube loaded sections formed in a tube cutting apparatus, a tube sealing apparatus which seals ends of a tube by fusion or the like, an apparatus for connecting an end of a tube to a connector or a needle. Further, the structure of the tube loaded section is also no limited to the groove described above. Any other structures such as a tube receiving section defined by frame-like members and a plurality of rod-like members can be adopted instead of the groove structure if these tube receiving sections can support a tube in contact with its outer surface.

Further, in the tube loading apparatus according to the present invention, it is possible to adopt the type in which the head is movable in X, Y and Z directions, the type in which the head is movable in arbitrary two directions among the three directions, the type in which the head is movable in arbitrary one direction among the three directions, or the type in which the head is not movable in any direction. In these cases, the tube loaded section or the carrier rail is constituted so as to be able to move toward the directions in which the head can not be moved, so that it becomes possible to load the tube into the tube loaded section. For example, in a case where the head is movable only in the X direction or in the X and Z directions, it becomes possible to load the tube into the tube loaded section if the tube loaded section can be moved in at least Y direction. Further, in a case where the head is movable only in Y direction or in Y and Z directions, it becomes possible to load the tube into the tube loaded section if the tube loaded section can be moved in at least X direction. Furthermore, in a case where the head is not movable in any one of the X, Y and Z directions, it becomes possible to load the tube into the tube loaded section if the tube loaded section can be moved in at least X and Y directions.

Finally, it should be noted that the present invention is no limited to the above described embodiment or the modifications. The scope of the present invention is determined only by the following claims.

What is claimed is:

1. A system for connecting one flexible tube to another flexible tube, comprising:

a tube receiving section for receiving a flexible tube;

a tube loading apparatus for loading the flexible tube into the tube receiving section, the tube loading apparatus including:

a first chuck for holding the flexible tube at a first point and a second chuck for holding the flexible tube at a second point which is spaced apart from the first point by a predetermined distance along a longitudinal extent of the flexible tube;

driving means for moving at least one of the chucks while the flexible tube is held by the chucks to change the distance between the chucks, increase a longitudinal length of the flexible tube and reduce an outer diameter of the flexible tube;

a head which is movable relative to the tube receiving section, said first and second chucks being provided on said head; and a head moving device for moving the head at least in the longitudinal direction of the flexible tube and in a direction perpendicular to the longitudinal direction of the flexible tube so that the flexible tube can be inserted into the tube receiving section; and a tube connecting device for connecting the flexible tube to another flexible tube, wherein said tube connecting device comprises said tube receiving section.

2. The system as claimed in claim 1, wherein said tube connecting device includes a heating element.

3. The system as claimed in claim 1, wherein each of said first and second chucks comprises a pair of holding members which is adapted to hold the tube therebetween.

4. The system as claimed in claim 3, wherein the holding members of each chuck include a tip portion having an angular shape defining an outwardly projecting apex.

5. The system as claimed in claim 3, wherein the holding members of each chuck include a generally C-shaped tip portion.

6. The system as claimed in claim 3, wherein the holding members of each chuck include a generally arc-shaped tip portion.

7. The system as claimed in claim 3, wherein one of the holding members of each chuck includes a generally C-shaped tip portion and the other holding member of each chuck is straight.

8. The system as claimed in claim 3, wherein one of the holding members of each chuck is generally arc shaped and the other holding member of each chuck is straight.

9. The system as claimed in claim 3, wherein the holding members of each chuck possess tip portions that are the same shape.

10. The system as claimed in claim 3, wherein the holding members of each chuck possess differently shaped tip portions.

* * * * *

UNITED STATES PATENT AND TRADEMARK OFFICE
CERTIFICATE OF CORRECTION

PATENT NO. : 5,518,575          Page 1 of 2
DATED      : May 21, 1996
INVENTOR(S) : Takahiko WATANABE It is certified that error appears in the above-indentified patent and that said Letters Patent is hereby corrected as shown below:

On the title page.
   Section [56], kindly add the following:

| | | |
|---|---|---|
| --1,708,141 | 4/1929 | Kepler |
| 1 235 840 | 6/1971 | United Kingdom |
| 753 641 | 7/1956 | United Kingdom |
| 0 639 384 | 2/1995 | Europe |
| 0 226 410 | 6/1987 | Europe |
| 38 20 543 | 12/1989 | Germany |
| 1 472 320 | 1/1967 | France |
| 2 401 011 | 12/1979 | France -- |

In Column 1, line 45, delete "tile" and insert -- the --.
In Column 1, line 47, delete "tile" and insert -- the --.
In Column 1, line 52, after "to" and before "tube" insert -- a --.
In Column 1, line 65, delete "tile" and insert -- the --.
In Column 3, line 36, delete "tile" and insert -- the --.
In Column 3, line 53, delete "X the" and insert -- the X --.
In Column 3, line 59, delete "tile" and insert -- the --.

UNITED STATES PATENT AND TRADEMARK OFFICE
CERTIFICATE OF CORRECTION

PATENT NO. : 5,518,575

DATED : May 21, 1996

INVENTOR(S) : Takahiko WATANABE

It is certified that error appears in the above-indentified patent and that said Letters Patent is hereby corrected as shown below:

In Column 4, line 32, delete "tile" and insert -- the --.
In Column 5, line 14, delete "tile" and insert -- the --.
In Column 5, line 35, after "design" delete "a".
In Column 7, line 11, delete "shaped" and insert -- u-shaped --.
In Column 9, line 42, delete "In" and insert -- in --.
In Column 10, line 20, delete "Is" and insert -- is --.

Signed and Sealed this

Fifteenth Day of October, 1996

Attest:

BRUCE LEHMAN

Attesting Officer   Commissioner of Patents and Trademarks